United States Patent [19]

Hollyday et al.

[11] 3,937,731

[45] Feb. 10, 1976

[54] IMINE DERIVATIVES OF ALKYLATED ARYL COMPOUNDS

[75] Inventors: William C. Hollyday, Plainfield; Shih-En Hu, Linden, both of N.J.

[73] Assignee: Exxon Research & Engineering Co., Linden, N.J.

[22] Filed: Jan. 14, 1972

[21] Appl. No.: 218,030

Related U.S. Application Data

[63] Continuation of Ser. No. 466,419, June 23, 1965, abandoned.

[52] U.S. Cl. .......... 260/566 F; 260/566 R; 252/150
[51] Int. Cl.² ........................................ C07C 119/00
[58] Field of Search ....... 260/566 R, 566 F, 268 TR

[56] References Cited
UNITED STATES PATENTS

| | | | |
|---|---|---|---|
| 2,282,513 | 5/1942 | Downing et al. | 260/566 R |
| 2,760,957 | 8/1956 | Adelson | 260/566 R |

*Primary Examiner*—Gerald A. Schwartz
*Attorney, Agent, or Firm*—Byron O. Dimmick; Frank T. Johmann

[57] ABSTRACT

Disclosed are Schiff base derivatives of acylated aromatic hydrocarbons useful as oil soluble additives having pour point depressing and sludge dispersing properties.

5 Claims, No Drawings

IMINE DERIVATIVES OF ALKYLATED ARYL COMPOUNDS

This is a continuation of application Ser. No. 466,419 filed June 23, 1965.

The present invention concerns certain metal-free additives that are capable of serving multiple functions in oleaginous compositions of the class of gasolines, fuel oils, heating oils, and lubricating oils. The invention is also directed to the preparation of these additives and to oleaginous compositions containing them. The additives may be characterized as oil-soluble imine or Schiff base derivatives of acylated aromatic hydrocarbons.

Crankcase oils for use in the lubrication of modern high compression piston type internal combustion engines must be of the heavy-duty detergent type. This requires that such oils contain additives that will impart good detergency, efficient sludge dispersing action, and high oxidation resistance. In the past, the required detergency and dispersancy have been supplied in heavy-duty internal combustion engine lubricants by using various metal compounds, such as metal salts of organic sulfonic acids, metal salts of alkylated phenols, metal salts of alkyl phenol thioethers, metal alcoholates, colloidal dispersions of metal carbonates and the like. In most cases, these salts are of alkaline earth metals. It has been more recently recognized that metal-free additives or at least additives that are relatively low in metal content are preferred to the conventional metal-containing additives. The metal-containing additives have the disadvantage of leaving an ash residue which tends to accumulate in the combustion chamber of the engine. This leads to spark plug fouling, valve burning, preignition, and similar undesirable conditions. It is evident that an effective dispersant that is ash-free is preferable to one that forms an ash, such as an alkaline earth metal salt of the several types mentioned above. Ash-free dispersants are also of advantage in diesel fuels and in fuel-oil compositions.

It has now been found in accordance with the present invention that highly effective ash-free, mineral-oil-soluble detergent inhibitors and dispersants that also possess pour-point-depressant properties can be prepared by reacting certain acylated derivatives of alkylated aromatic hydrocarbons with aliphatic polyamines. It is believed that the materials that are thereby obtained are imines or Schiff bases of the general formula:

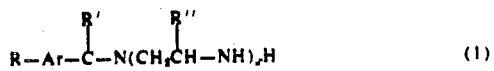

(1)

wherein R is selected from the group consisting of hydrogen and aliphatic hydrocarbon radicals having in the range from 12 to 40 carbon atoms; Ar is an aromatic group derived from an aromatic hydrocarbon of the group consisting of benzene, naphthalene, anthracene, and phenanthrene; R' is selected from the group consisting of hydrogen, alkyl radicals of 1 to 10 carbon atoms, aralkyl radicals of 7 to 10 carbon atoms, and alkylene radicals of about 12 to 40 carbon atoms linking another Ar group, R' being such an alkylene radical at least where R is hydrogen; R'' is selected from the group consisting of hydrogen and $C_1$ to $C_3$ alkyl groups, and X is a number from 1 to about 10.

The starting materials for the preparation of the acylated derivatives from which the imine compounds are derived may be alkylated aromatic compounds prepared by alkylating such hydrocarbons as benzene, naphthalene, anthracene, or phenanthrene with a halogenated paraffinic hydrocarbon of the $C_{12}$ to $C_{40}$ range, for example, chlorinated dodecane, brominated cetane, chlorinated gas oil, chlorinated kerosene, and the like. A particularly useful alkylating material is halogenated paraffin wax, and a particularly useful starting material is wax-alkylated naphthalene. While aromatic hydrocarbons can also be alkylated with olefins, e.g., a propylene polymer or an isobutylene polymer, in the presence of suitable catalysts, alkylation with halogenated paraffinic hydrocarbons is usually less expensive. Also diolefins and polyfunctional olefins of suitable high chain length are not readily available, so that the linking of two or more aromatic nuclei that is possible through a polyhalogenated aliphatic hydrocarbon cannot be as conveniently duplicated by alkylation with olefins. Naturally-occurring alkylated aromatic hydrocarbons of sufficiently high molecular weight for use in this invention are also available. One source of such hydrocarbons are the heavy lubricating oil residual fractions known as bright stocks.

To introduce acyl groups into the alkylated aromatic hydrocarbon, the latter may be treated with an anhydride of a monobasic acid, such as acetic anhydride, or with an acyl halide, such as acetyl chloride or benzoyl chloride, in the presence of a Friedel-Crafts catalyst. Alternatively, the acyl group can be introduced by oxidation of the alkylated aromatic hydrocarbon.

The acyl halides that are employed for the acylating reaction are preferably those derived from aliphatic or arylated aliphatic monocarboxylic acids of from 2 to 10 carbon atoms. The resulting acylated aromatic hydrocarbons will have the general formula:

(2)

wherein R is at least one aliphatic hydrocarbon radical, having in the range from 12 to 40 carbon atoms, R' is the hydrocarbon residue of the acyl halide that was used, and Ar is an aromatic group as previously defined.

In the alkylation of the aromatic hydrocarbon with a halogenated aliphatic hydrocarbon, such as chlorinated paraffin wax, it is possible to have two or more aromatic nuclei joined by aliphatic hydrocarbon linkages so that the acyl derivative could have a formula of the following nature:

(3)

wherein R can be hydrogen or an aliphatic radical of from 12 to 40 carbon atoms; R' may be hydrogen or an alkyl radical of from 1 to 6 carbon atoms; $x$ is a number of from 10 to 40 and $n$ is a number from 1 to 10, and Ar is as previously defined.

It is also possible to have a structure wherein not all of the aryl groups are acylated, as for example in the general structure shown below:

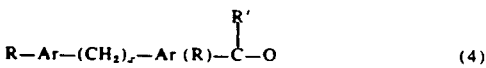

(4)

In the above formula, R', Ar, and x have the same significance as in formula (3).

When acylation is effected by oxidation of the alkylated aromatic hydrocarbon, it is believed that ketone formation occurs with some of the alkyl groups. For example, wax alkylated naphthalene is considered to consist of two or more naphthalene nuclei linked by aliphatic hydrocarbon linkages derived from the chlorinated paraffin wax as represented by the following formula:

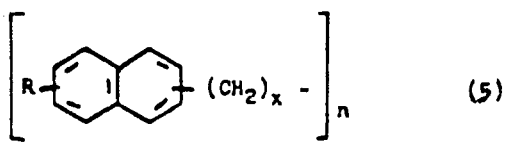

(5)

R, x, and n having the same significance as in the preceding formulas. Upon oxidation, ketones are formed, which may be represented by the following formula:

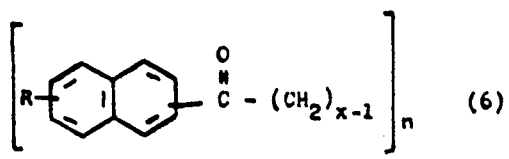

(6)

The preparation of alkylated aromatic hydrocarbons by the Friedel-Crafts condensation with halogenated aliphatic hydrocarbons is well known. Alkylation of naphthalene in this manner is disclosed, for example, in U.S. Pat. Nos. 1,815,022 and 2,015,748. Briefly, the reaction involves the halogenation, (preferably chlorination) of an aliphatic hydrocarbon of from about 12 to about 40 carbon atoms until the product contains about 10 to 15 wt. % of chlorine. The halogenated material is then condensed with naphthalene in the presence of aluminum chloride or similar Friedel-Crafts catalysts. For example, paraffin wax or petrolatum may be chlorinated at a temperature in the range of 140° to 300°F. until it contains 10 to 14 per cent chlorine and it may then be condensed with naphthalene at 100° to 160°F. with the aid of a Friedel-Crafts catalyst. As a specific example, 9 parts of chlorinated wax can be condensed with one part of naphthalene, using as a catalyst one part by weight of aluminum chloride.

As previously stated, one method that can be used for acylating an alkylated condensed ring aromatic hydrocarbon is to react it with an acid anhydride or with an acyl halide, such as acetyl chloride. This condensation is conducted with the aid of a Friedel-Crafts catalyst, such as aluminum chloride or boron fluoride. Generally, from about 0.1 to 1.0 mole of acid anhydride or of acyl halide is used per aromatic group that is to be acylated, although greater than 1 mole may be used in some instances. The amount of Friedel-Crafts catalyst used will generally be in the range of about 0.1 to 2.0 moles per mole of acyl halide or acid anhydride. Temperatures may range from about 60° to about 180°F., more generally about 70° to 150°F. Reaction times will be in the range of about 0.5 to 5 hours, or more generally about 1 to 3 hours.

It is possible to conduct the steps of alkylating the condensed ring aromatic hydrocarbon and the step of converting the alkylated material to an acylated product in one operation, i.e., by reacting the aromatic hydrocarbon with the alkylating agent, such as chlorinated wax and with the acylating agent, e.g., the acyl halide in the presence of a Friedel-Crafts catalyst.

As stated above, carbonyl groups can also be introduced into the alkylated aromatic hydrocarbon by an oxidation reaction. The oxidation may be effected with mild oxidizing agents or by the use of air or other oxygen-containing gas mixtures in the presence of suitable catalysts. The latter include oxides of manganese, selenium, chromium and $C_1$ to $C_5$ fatty acid salts of such metals, e.g., manganese acetate. Oxidation by air blowing may be conducted at temperatures ranging from about 160°F. to about 480°F. for from about 2 to 48 hours in the presence of 0.2 to 10 wt. % catalyst; preferably at 250°F. to about 350°F. for 6 to 24 hours in the presence of 0.5 to 5 wt. % of catalyst.

To prepare the additives of the present invention the acylated, alkylated aromatic hydrocarbon is condensed with an alkylene polyamine. One or more amino groups of the alkylene polyamine react with a carbonyl group in the acylated hydrocarbon to form a Schiff base derivative of the general nature represented by formula (1) above. Generally, the mole ratio of polyamine to acylated hydrocarbon will range from about 0.2 to about 1.5, although it is preferred that this ratio be in the range from about 0.5 mole of polyamine per carbonyl group up to about 1.0 mole of polyamine per carbonyl group. The reaction temperatures will generally be in the range of from about 140° to about 350°F. In most cases, however, a narrower range from about 180° to about 240°F. will be used. The reaction time will depend to some extent upon the reaction temperature. The composition of the reaction can be determined by measuring the amount of water that is split off during the reaction. It is usually advantageous to employ a water-entraining solvent, such as heptane, benzene, or toluene to remove the water as an azeotrope. The reaction may require from 1 to 48 hours but will usually be complete in from 2 to 12 hours.

In certain instances there may be a tendency for cross-linking between the polyamine and the acylated hydrocarbon which may tend to impair the oil-solubility of the product. Also in some instances it may be desirable to adjust the dispersancy potency of the reaction product by blocking off some of the amino groups of the polyamine. Accordingly, it is an added feature of the present invention to control oil-solubility and dispersant action by further reaction and/or by concomitant reaction with lower molecular weight ketones, preferably those having from 3 to 6 carbon atoms, including acetone, methyl ethyl ketone and methyl isobutyl ketone. The lower ketone may be mixed with the acylated aromatic hydrocarbon at the start of the reaction, or at a later stage during the reaction or subsequent to the reaction of the polyamine with the acylated aromatic hydrocarbon. If during the reaction of the polyamine and the acylated hydrocarbon it is noted either by visual observation or by viscosity measurements that cross-linking is occurring, a lower ketone may be added to the reaction mixture to prevent further cross-linking. The amount of lower ketone thus added may be from 0.1 to 1 mole for each amino group in the polyamine in excess of the amino groups contemplated for reaction with the carbonyl groups of the acylated aromatic hydrocarbon.

The aliphatic polyamine that is employed in preparing the reaction products of the present invention may be an alkylene polyamine fitting the following general formula:

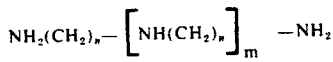

wherein $n$ is 2 to 4 and $m$ is a number from 0 to 10. Specific compounds coming within the formula include diethylene triamine, tetraethylene pentamine, dibutylene triamine, dipropylene triamine, octaethylene nonamine, and tetrapropylene pentamine. N,N-di-(2-aminoethyl) ethylene diamine may also be used. Other aliphatic polyamine compounds that may be used include the N-aminoalkyl piperazines of the formula:

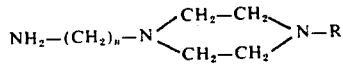

wherein $n$ is a number 1 to 3, and R is hydrogen or an aminoalkyl radical containing 1 to 3 carbon atoms. Specific examples include N-(2-aminoethyl) piperazine, N-(2-aminoisopropyl) piperazine, and N,N'-di-(2-aminoethyl) piperazine.

Still other alkylene amino compounds that may be used include dialkylamino alkyl amines such as dimethylamino methyl amine, dimethyl amino propyl amine, methyl propyl amino amyl amine, etc. These may be characterized by the formula:

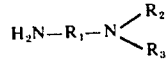

wherein $R_1$ is an alkylene radical, e.g., an ethylene, propylene, or butylene radical, and $R_2$ and $R_3$ are $C_1$ to $C_5$ alkyl radicals.

Thus the alkylene polyamine or aliphatic polyamine compounds used in this invention may be broadly characterized as alkylene amino compounds containing 2 to 12 nitrogen atoms wherein pairs of nitrogen atoms are joined by alkylene groups of from 2 to 4 carbon atoms.

The use of mixtures of alkylene polyamines, dialkylamino alkyl amines, mixtures of N-aminoalkyl piperazines, and mixtures of the alkylene polyamines with the N-aminoalkyl piperazines is also contemplated.

The nature of this invention will be further understood when reference is made to the following examples:

EXAMPLE 1

The starting material for the preparation of an acylated aromatic hydrocarbon was a 50 wt. % concentrate of a wax-alkylated naphthalene in a solvent neutral mineral oil (viscosity 150 SUS at 100°F.). The wax-alkylated naphthalene had been obtained by chlorinating a crude paraffin wax of 125°F. melting point to a chlorine content of 14.5 wt. % and condensing 12 parts by weight of naphthalene with 100 parts of the chlorinated wax with the aid of aluminum chloride catalyst.

A complex was prepared by adding 39 grams of acetyl chloride to 66 grams of anhydrous aluminum chloride with stirring. To this mixture was then added 150 grams of the 50 wt. % concentrate of wax alkylated naphthalene described above. The mixture was stirred at 70° to 75°F. for three hours. During this time, a precipitate of a complex of the resulting acylated material and aluminum chloride was formed. This precipitate was separated from the supernatent oily layer and then treated with water to decompose the aluminum chloride. A yield of 73 grams of acylated material was obtained. Direct analysis indicated that the material contained 3.24 wt. % of oxygen. This was found by calculation to be equivalent to 2 gram moles of carbonyl groups per 1,000 grams of product.

A mixture was prepared consisting of 50 grams of the acylated product obtained as above, 10.5 grams of diethylene triamine, and 70 ml. of benzene. This mixture was heated under reflux until 1.5 ml. of water was collected in the reflux trap. Then 12 grams of acetone was added to the mixture and refluxing was continued until an additional 3.6 ml. of water was collected.

The final product, which amounted to 66 grams, was treated with methanol to separate it into methanol-soluble and methanol-insoluble fractions. There was obtained 58 grams of a methanol-insoluble, oil-soluble additive concentrate fraction containing 4.07 per cent nitrogen.

EXAMPLE 2

An acylated product of an alkylated naphthalene was prepared by a single-step process in the following manner. A solution of 25.6 grams of naphthalene in 38 ml. of o-dichlorobenzene was added to a mixture of 6 grams of $AlCl_3$ and 200 grams of chlorinated wax of 14.5 wt. % chlorine content derived from 125° melting point paraffin wax. This mixture was maintained at a temperature of 145° to 150°F. for four hours. Then an additional 66 grams of aluminum chloride was added. The temperature was maintained at 118° to 120°F. while 51 g. of acetic anhydride was gradually added. After 4 hours, the mixture was mixed with 200 ml. of water to remove $AlCl_3$. The water phase was separated and discarded, and the organic phase was washed with three separate 200 ml. portions of water. Dichlorobenzene was stripped from the product at 248°F. (20 mm. Hg pressure). The resulting product weighed 200 grams and analyzed 2.92 % oxygen. The latter product was blended to 50 wt. % concentration in a light mineral lubricating oil. Then 200 grams of the concentrate, 16 grams of tetraethylene pentamine, and 200 grams of heptane was refluxed for 12 hours, during which time 1.5 ml. of water was collected in the reflux trap. The heptane was then stripped from the reaction product. Yield was 200 grams of concentrate analyzing 2.21 wt. % nitrogen.

EXAMPLE 3

The starting material for this example is a 50 wt. % concentrate of a wax alkylated naphthalene in a solvent neutral mineral oil, the oil having a viscosity of 150 SUS at 100°F. The wax alkylated naphthalene is made in a manner similar to that used in Example 1, except that it is prepared by alkylating 20 parts by weight of naphthalene with 100 parts of chlorinated wax obtained by chlorinating a wax of 108°F. melting point to 20 wt. % chlorine. As in Example 1, a complex is first prepared by mixing 39 grams of acetyl chloride with 66 grams of anhydrous aluminum chloride. To this is added 152 grams of the wax alkylated naphthalene concentrate. The acylation is performed by stirring this mixture for three hours at 70° to 75°F. The resulting product is hydrolyzed with water and then worked up in a manner similar to that used in Example 1. The yield of acylated material is 118 grams. The acylate contains 5.34 wt. % oxygen by direct analysis, this being equivalent to 3.34 gram moles of carbonyl groups per 1,000 grams of product.

A mixture of 400 grams of the acylate, 400 grams of heptane and 32 grams of tetraethylene pentamine is heated under reflux for 12 hours, 3 grams of water being released from the reaction mixture and collected overhead on the reflux trap. The heptane is then removed from the product.

EXAMPLE 4

A suspension of 10 grams of manganese acetate was prepared in 250 grams of the same wax alkylated naphthalene concentrate used in Example 1. Air was passed through this mixture for 7 hours at about 250°F. Catalyst was then removed from the product by filtration. The yield of product was 220 grams. Strong carbonyl bands at 5.85μ were found upon infrared analysis.

The entire oxidized product was dissolved in 200 ml. of heptane and mixed with 20 grams of tetraethylene pentamine. The resulting mixture was heated under reflux for 12 hours during which time 2 ml. of water was collected in the reflux trap. The reaction product was filtered and then stripped of heptane. Yield of product was 220 grams. Analysis of the 50 wt. % concentrate showed 2.02 wt. % nitrogen.

EXAMPLE 5

A solution was prepared by dissolving in 100 ml. of carbon tetrachloride 200 g. of the same wax alkylated naphthalene concentrate that was used in Example 1. This solution was then treated at room temperature with 20 g. bromine added dropwise over a period of 30 minutes. The resulting brominated product was hydrolyzed with 100 ml. of water on a steam bath for 3 hours. Completion of the hydrolysis step was determined by periodic infrared analysis of withdrawn samples, the end point being indicated by there being no further increase in intensity at 5.8 millimicrons. After the hydrolyzed product was separated from the water, it was mixed with 100 ml. of toluene and 20 ml. of tetraethylene pentamine. This mixture was then heated under reflux and the water of condensation was removed as an azeotrope with the toluene. Completion of the reaction was indicated when no additional water came over with the toluene. The carbon tetrachloride was then removed from the product by evaporation. The product was analyzed and found to contain 1.5 wt. % of nitrogen.

EXAMPLE 6

A mixture was prepared consisting of 400 g. of the wax alkylated naphthalene concentrate of Example 1, 27 g. of aluminum chloride, and 200 ml. of ortho-dichlorbenzene. Then while the temperature was raised from room temperature to about 140°f., 55 g. of benzoyl chloride was added gradually with stirring. The temperature was held at 140°F. for five hours. Thereafter, to decompose the aluminum chloride complex 200 ml. of hydrochloric acid (0.5 N) was added and the reaction mixture was washed three times with water using 200 ml. of water in each wash. The solvent was then removed from the acylation product by vacuum distillation (15 mm. Hg.) at 250°F. Then 400 g. of the acylation product was dissolved in 300 ml. of heptane and 28 g. of tetraethylene pentamine was added. Heating was conducted under reflux under conditions enabling the removal of water of condensation as an azeotrope with the heptane, completion of the reaction being determined by the fact that no additional water was carried over with the heptane. The remaining heptane was then removed from the product by evaporation in a steam bath. The product contained 3.18 wt. % nitrogen by analysis on an active ingredient base, i.e., excluding the diluent oil in the original wax alkylated naphthalene concentrate.

EXAMPLE 7

A solution was prepared consisting of 100 ml. of ortho-dichlorobenzene and 56 g. of a petroleum bright stock which had a viscosity of 529.2 cs. at 100°F. and a viscosity of 32.6 cs. at 210°F. To this was added 3 g. of anhydrous aluminum chloride followed by 22 g. of n-1-hexadecone added over a period of 30 minutes. After reaction was continued at 85° to 100°F. for an additional 30 minutes, 12 additional g. of aluminum chloride was added over a 10-minute period followed by 8.5 g. acetyl chloride. After the mixture was stirred at 85° to 95°F. for an additional 30 minutes, the temperature was increased to about 125°F. and held there for three hours. At the end of this time the reaction mixture was diluted with about 150 ml. hexane and then washed several times with water, the amount of water in each instance being about equal in volume to the mixture being washed. The yield of acylated product after removal of solvents on the steam bath was 80.6 g.

This acylated product contained some unreacted olefin and some low molecular weight olefin polymer as well as the desired alkylated/acylated bright stock. Then 50 g. of this crude acylated product was reacted with 7 g. of tetraethylene pentamine by refluxing in the presence of 200 g. of benzene with provision for separating the water which came over with the benzene, refluxing being continued until no more water was carried over. The product was found to consist of 1.8 g. of unreacted tetraethylene pentamine and 54.7 g. of oil-soluble material containing 2.75% nitrogen.

EXAMPLE 8

To a solution of 56 g. of the same bright stock as in Example 7, in 100 ml. of ortho-dichlorobenzene, 15 g. of anhydrous aluminum chloride was added, followed by a mixture of 8 g. of acetyl chloride and 22 g. of n-1-hexadecene over a period of 30 minutes. During this time the temperature rose from about 78°F. to about 125°F. Reaction was continued at the latter temperature for three hours with stirring and heating. Thereafter, the product was treated in the same manner as in Example 7, i.e., diluted with hexane, washed with water, heated to remove solvents, and then reacted with tetraethylene pentamine in the same proportions as in Example 7. The final oil-soluble product contained 3.79% nitrogen.

EXAMPLE 9

A complex of acetyl chloride and aluminum chloride was prepared by mixing the two materials in equimolar proportions. Then 211 grams of this complex was added to 1,000 grams of the same bright stock that was used in Example 7. The mixture was heated with stirring at 75° to 80°F. for four hours and then for an additional hour at 195° to 200°F. for one hour. There were formed two layers, one being a supernatant oil layer and the other a precipitated complex mixture. The supernatant oil layer was decanted off and the complex was washed with hexane and then decomposed with cold water to remove the aluminum chloride. After further water washing and removal of hexane there was obtained 80.9 grams of acylated product analyzing 84.82% carbon, 11.76% hydrogen, and 3.42% oxygen (equivalent to 9.2 wt. % of acetyl groups). The original bright stock had a V. I. of 98, while the supernatant oil had a V. I. of 111, indicating that an important by-product of this phase of the invention is that the portion of the original lubricant stock that is not converted to additive is recoverable as an improved lubricant stock.

A mixture of 50 grams of the acylated product obtained as just described (0.107 gram atom of oxygen), 11 grams of diethylene triamine (0.107 gram mole) and 70 ml. of benzene was heated under reflux until 1.2 ml. of water was removed overhead. Then 12 g. (0.207 mole) of acetone was added and refluxing was continued until 2.6 additional ml. of water was collected. The product amounting to 64.8 grams was separated into methanol-soluble and methanol-insoluble portions. The latter portion consisted of 53 grams of an oil-soluble detergent dispersant product containing 3.06 wt. % nitrogen.

EXAMPLE 10

Using as the base oil a mineral lubricating oil having a viscosity of 325 SSU at 100°F. and a viscosity index of about 100, a reference blend was prepared by simple mixing of 3.5 wt. % of a commercial detergent inhibitor, 0.9 wt. % of a zinc dialkyldithiophosphate antiwear additive and 95.6 wt. % of the base oil.

Test compositions were prepared by simple mixing of 3.5 wt. % of the same detergent inhibitor, 0.9 wt. % of the same antiwear additive and 93.6 wt. % of the same base oil as in the reference blend along with 2 wt. % of the products of Examples 1, 4, 5, and 6 respectively. In each instance this furnished sufficient additive to give 1 per cent active ingredient.

The commercial detergent inhibitor mentioned above was a mineral oil solution containing an additive prepared by reacting a mixture of a phosphosulfurized polyisobutylene and nonyl phenol with barium hydroxide pentahydrate and blowing the reaction mixture with carbon dioxide. The approximate analysis of the concentrate was 27 wt. % of phosphosulfurized polyisobutylene, 11.7 wt. % nonyl phenol, 10.6 wt. % barium oxide, 2.5 wt. % carbon dioxide, and 48.2 wt. % of mineral oil.

The zinc dialkyldithiophosphate antiwear additive was an oil solution consisting of about 25 wt. % of mineral lubricating oil and about 75 wt. % of zinc dialkyldithiophosphate prepared by treating a mixture of isobutanol and mixed amyl alcohols with $P_2S_5$ followed by neutralizing with zinc oxide.

Each of the compositions was tested for sludge dispersing ability in a Cyclic Temperature Sludge Test which, from prior experience, has been shown to give sludge deposits similar to those obtained in stop-and-go driving such as would be experienced in taxicab operation. Briefly described, in this test a Ford 6-cylinder engine is run on a dynamometer stand through alternate cycles, the first cycle lasting 5 hours, at 1500 rpm, and the second cycle lasting 2 hours, at the same operating speed, with the oil pump and water jacket temperatures being slightly higher in the second cycle than in the first. The two cycles are alternated in sequence until the desired total test time has elapsed. Make-up oil is added as required so as to maintain the oil level in the crankcase at all times between about 3½ and 4 quarts. At the end of selected periods of test time, the engine is inspected by disassembling it sufficiently to permit visual examination of several of the parts, including the rocker arm assembly, the rocker arm cover, the cylinder head, the push rod chamber and its cover, the crankshaft and the oil pan. These parts are visually and quantitatively rated for sludge deposits, using a CRC Sludge Merit rating system in which a numerical rating of 10 represents a perfectly clean part, and the numerical scale decreases to a minimum value representing a part covered with the maximum amount of sludge possible. The several merit ratings are averaged to give an overall engine merit rating.

The results of the cyclic temperature sludge test are summarized in Table I. It will be seen from these results that incorporation of the additive products of the present invention greatly increased the ability of the oil composition to disperse sludge.

TABLE I

Sludge Merit Ratings - Cyclic Temperature Test

| Test Hours | Reference Blend | Composition Reference Blend Plus Additive of | | | |
|---|---|---|---|---|---|
| | | Ex. 1 | Ex. 4 | Ex. 5 | Ex. 6 |
| 42 | 8.6 | 9.98 | — | — | — |
| 63 | 6.9 | 9.95 | 9.63 | 9.91 | — |
| 84 | 5.8 | 9.66 | 8.2 | 9.81 | 9.93 |
| 105 | — | 9.3 | 6.9 | 9.51 | 9.75 |

EXAMPLE 11

A fully formulated motor oil having excellent detergency, dispersancy, pour-point, and viscosity properties and excellent resistance to viscosity loss under shearing conditions is prepared by blending together 4.6 wt. % of the commercial detergent inhibitor described in Example 10, 1.3 wt. % of the zinc dialkyldithiophosphate antiwear additive described in Example 10, 2.5 wt. % of a 45 wt. % concentrate of a high alkalinity barium synthetic sulfonate having 14.5% barium and having a total base number of 59, 2 wt. % of the product of Example 1, 1.4 wt. % of a viscosity index improver, 60 wt. % of a mineral lubricating oil having a viscosity of 114 SSU at 100°F., and 40.7 SSU at 210°F. and 23.4 wt. % of a mineral oil having a viscosity of 396

SSU at 110°F. and 59.0 SSU at 210°F. The viscosity index improver comprises a copolymer of about 40,000 molecular weight composed of about 50 mole per cent of vinyl acetate, about 44 mole per cent of $C_8$ oxo alcohol fumarates and about 6 mole per cent of the fumarates of tallow alcohols (mixed n-hexadecyl fumarate and n-octadecyl fumarate in about 2:3 mole ratio).

This blend has the following properties:

| | |
|---|---|
| Pour Point °F. | −30 |
| Viscosity SUS at 210°F. | 59 |
| Viscosity Index | 138 |

EXAMPLE 12

A lubricant composition suitable for use as a railroad diesel engine lubricant is prepared by blending 2.0 wt. % of the concentrate additive of Example 6 and 0.4 wt. % of phenyl alpha naphthylamine in a base stock consisting of a hydrofined and phenol extracted coastal distillate having a viscosity of 1070 SSU at 100°F. and a viscosity of 78.8 SSU at 210°F.

EXAMPLE 13

A high detergency lubricating oil of SAE 10W-30 viscosity rating was prepared by blending 67 vol. % of a solvent neutral mineral lubricating oil of 100 SSU viscosity at 100°F., 15 vol. % of refined mineral lubricating oil of 396 SSU viscosity at 110°F. and 59 SSU viscosity at 210°F., 10 vol. % of a 20 vol. % concentrate of 15,000 molecular weight polyisobutene V. I. improver, 5 vol. % of the commercial detergent inhibitor concentrate and 1 vol. % of the antiwear additive concentrate described in Example 9, and 2 vol. % of the barium sulfonate concentrate described in Example 11. To a portion of this blend was added sufficient of the product of Example 1 to provide 1 wt. % of additive. The blend without the additive of Example 1 had a pour point of +30°F. The blend containing the additive of Example 1 had a pour point of −30°F.

EXAMPLE 14

To a heating oil comprising a mineral oil distillate having a boiling range of about 350° to 680°F. and derived from mixed cracked and straight run distillates is added 0.06 wt. % of the concentrate product of Example 3. The pour point of the heating oil is thereby lowered from −5°F. to −10°F. If 0.08 wt. % of the additive concentrate is employed, the pour point of the heating oil is lowered to −15°F.

EXAMPLE 15

About 0.008 wt. % of the concentrate of Example 5 is added to a leaded gasoline for the purpose of imparting rust preventive properties and carburetor detergency action thereto.

The additives of this invention may be employed in concentrations ranging from about 0.002 to about 10 wt. % in oleaginous compositions ranging from gasoline fractions through middle distillate fuels and lubricating oils.

For use as lubricating oil additives the reaction products of this invention may be incorporated in lubricating oil compositions in concentration ranges of from about 0.1 to about 10 wt. % on an actual ingredient basis, and will ordinarily be used in concentrations of from about 0.1 to about 5 wt. %. The lubricating oils to which the additives of the invention may be added include not only mineral lubricating oils, but synthetic oils also. The mineral lubricating oils may be of any preferred types, including those derived from the ordinary paraffinic, naphthenic, asphaltic, or mixed base mineral crude oils by suitable refining methods. Synthetic hydrocarbon lubricating oils may also be employed. Other synthetic oils include dibasic acid esters such as di-2-ethyl hexyl sebacate, carbonate esters, phosphate esters, halogenated hydrocarbons, polysilicones, polyglycols, glycol esters such as $C_{13}$ oxo acid diesters of tetraethylene glycol, and complex esters as for example the complex ester formed by the reaction of 1 mole of sebacic acid with 2 moles of tetraethylene glycol and 2 moles of 2-ethyl hexanoic acid.

The additives of this invention may also be employed in middle distillate fuels for inhibiting corrosion and the formation of sludge and sediment in such fuels. Concentration ranges of from about 0.002 to about 2 wt. % or more, generally from about 0.005 to about 0.2 wt. %, are employed. Petroleum distillate fuels boiling in the range of from about 300° to about 900°F. are contemplated. Typical of such fuels are No. 1 and No. 2 fuel oils that meet ASTM Specification D-396-48T, diesel fuels qualifying as Grades 1D, 2D and 4D of ASTM Specification D-975-51T, and various jet engine fuels. Because they are ashless, these additives are particularly desirable for such fuels in that they do not give rise to glowing ashes nor deter from the burning qualities of the distillates. These additives may also be used in conjunction with other prior art ashless additives for fuels, such as polymers of acrylic or methacrylic acid esters, high molecular weight aliphatic amines, etc.

The additives of this invention may also be employed either alone or in combination with other hydrocarbon-soluble additives, in jet fuels and gasolines in concentrations ranging from about 0.001 to 1.0 wt. % as detergent and/or rust preventive additives.

In either the fuel or lubricant compositions, other conventional additives may also be present, including dyes, pour-point depressants, antiwear agents, e.g. tricresyl phosphate, zinc dialkyl dithiophosphates of 3 to 8 carbon atoms, antioxidants such as phenyl-alpha-naphthylamine, tert. octylphenol sulfide, bis-phenols such as 4,4'-methylene bis (2,6-di tert. butylphenol), viscosity index improvers such as polymethacrylates, polyisobutylene, alkyl fumarate-vinyl acetate copolymers, and the like, as well as other dispersants.

The dispersant additives of the invention may be employed to enhance the dispersancy-detergency of lubricants containing conventional detergents, wherein the latter are used in concentrations in the range of about 0.5 to 5 wt. %. When the conventional detergents or dispersants are metal-containing materials it is possible, by utilizing the additives of the present invention in combination therewith, to obtain added dispersancy or detergency without materially increasing the total ash-forming properties of the composition. Such metal-containing detergents or combination detergent-inhibitors include the alkaline earth metal salts of alkylated phenols or of alkylated phenol sulfides, as for example barium-calcium nonyl phenol sulfide, the so-called basic earth metal sulfonates, and dispersions of barium carbonate or calcium carbonate in mineral oils containing various surfactants such as phosphosulfurized polyolefins, for example.

The sulfonates are well known in the art and are the oil-soluble alkaline earth metal salts of high molecular weight sulfonic acids obtained by sulfonating either natural or synthetic hydrocarbons. Specific examples of suitable sulfonates include calcium petroleum sulfonate, barium petroleum sulfonate, calcium di-$C_9$ alkyl benzene sulfonate ($C_9$ group from tripropylene), and barium $C_{16}$ alkyl benzene sulfonate ($C_{16}$ group from tetraisobutylene). The sulfonates may be of either the neutral type or of the "over-based" or "high alkalinity" type, containing metal base in excess of that required for simple neutralization, wherein the excess metal base has been neutralized with carbon dioxide.

Metal salts of alkyl phenols and of the alkyl phenol sulfides are also well known in the art. Metal salts of alkyl phenols having alkyl groups of from 5 to 20 carbon atoms are usually preferred, and the metal used to form the phenate in preferably an alkaline earth metal, e.g., calcium or barium, although the salts such as those of aluminum, cobalt, lead or tin are sometimes used. A specific example is the barium salt of the alkylation product of phenol with tripropylene. Metal salts of the corresponding alkyl phenol sulfides may also be used, e.g., barium tert. octyl phenol sulfide.

Other detergent additives include the reaction products of phosphosulfurized hydrocarbons with alkaline earth metal oxides or hydroxides which can be prepared by first treating a hydrocarbon with a phosphorus sulfide and then reacting the product with an alkaline earth metal hydroxide or oxide, for example barium hydroxide, preferably in the presence of an alkyl phenol or an alkyl phenol sulfide and also preferably in the presence of carbon dioxide.

The dispersants of this invention may also be used in conjunction with other ashless detergents or dispersants such as high molecular weight polymeric dispersants made with one or more polar monomers, such as vinyl acetate, vinyl pyrrolidone, methacrylates, fumarates and maleates. These dispersants have molecular weights in the range of about 500 to 50,000. One example is a copolymer of 65 to 85 wt. % of mixed $C_9$ to $C_{12}$ fumarates, 10 to 20 wt. % of vinyl acetate, and 5 to 15 wt. % of N-vinyl pyrrolidone. Another example is the copolymer derived by reaction of mixed tallow alcohol fumarates and $C_8$ oxo alcohol fumarates, averaging about 420 molecular weight, with vinyl acetate in a 3 to 1 acetate-fumarate ratio, and 3 wt. % of maleic anhydride, followed by subsequent removal of excess vinyl acetate. By tallow alcohol fumarates is meant that esters of fumaric acid and the alcohols derived by hydrogenation of tallow. The latter are principally $C_{16}$ and $C_{18}$ aliphatic alcohols with minor amounts of $C_{12}$, $C_{14}$ and $C_{20}$ alcohols. $C_8$ oxo alcohols are prepared by reaction of carbon monoxide and hydrogen on mixed $C_3$ to $C_4$ olefins followed by hydrogenation of the resulting aldehydes.

It is within the comtemplation of this invention to prepare additive concentrates in which the concentration of additive is greater than would normally be employed in a finished lubricant. These concentrates may contain in the range of from 10 to 80% of additive on an active ingredient basis, the balance being a hydrocarbon oil, usually a mineral oil. Such concentrates are convenient for handling the additive in the ultimate blending operation into a finished lubricating oil composition. The additive concentrates may be made up simply of an additive of the present invention in a suitable mineral oil medium or they may include other additives that are intended for use along with the additives of the invention in a finished lubricant. Thus, if the additives are to be used in conjunction with conventional detergents, an additive concentrate can be prepared containing say 30 to 60 wt. % of an additive of the invention and 5 to 20 wt. % of a metal sulfonate, e.g., calcium petroleum sulfonate from sulfonic acids of about 450 molecular weight, or a metal alkylphenol sulfide, e.g., calcium nonylphenol sulfide, with the balance being a mineral lubricating oil. Additionally, 5 to 15 wt. % of an antiwear agent such as a zinc dialkyldithiophosphate, e.g., mixed zinc butyl and amyl dithiophosphates may also be present in the additive concentrate package.

While the lubricant compositions herein described are primarily designed as internal combustion engine crankcase lubricants, the additives of the invention may also be employed in other oil compositions, including turbine oils, various industrial oils, gear oils, hydraulic fluids, transmission fluids and the like.

It is to be understood that the examples presented herein are intended to be merely illustrative of the invention and not as limiting it in any manner; nor is the invention to be limited by any theory regarding its operability. The scope of the invention is to be determined by the appended claims.

What is claimed is:

1. An oil-soluble additive having pour point depressing and sludge dispersing properties when added to a mineral lubricating oil, which comprises the product obtained by condensing a ketone, obtained by acylation of wax-alkylated naphthalene, with an alkylene polyamine at a temperature of from about 140° to 350°F. for a sufficient period of time to split out water and form a Schiff base and wherein:

said wax-alkylated naphthalene is the condensation product of naphthalene with a chlorinated paraffin wax of 12 to 40 carbon atoms chlorinated to about 10 to about 15 wt. % chlorine, wherein from about 9 parts of chlorinated paraffin wax is condensed per part of naphthalene, to about 100 parts by weight of chlorinated paraffin wax is condensed per 20 parts by weight of naphthalene, said acylation being effected by mild oxidation by air blowing at temperatures in the range of about 160° to 480°F. for about 2 to 48 hours, of said wax-alkylated naphthalene, or by reaction with in the range of about 0.1 to about 1.0 molar proportion of an acyl halide or acid anhydride of a $C_2$ to $C_{10}$ monocarboxylic acid per molar proportion of wax-alkylated naphthalene, said alkylene polyamine having 2 to 12 nitrogen atoms, and wherein pairs of nitrogen atoms are joined by alkylene groups of 2 to 4 carbon atoms, and in the range of about 0.2 to about 1.5 molar proportion of polyamine is condensed per molar proportion of acylated wax-alkylated naphthalene.

2. Oil-soluble additive as defined by claim 1, wherein said ketone is the product of acylating wax-alkylated naphthalene with acetyl chloride.

3. Oil-soluble additive as defined by claim 1, wherein said ketone is the product of acylating wax-alkylated naphthalene with acetic anhydride.

4. Oil-soluble additive as defined by claim 1, wherein said aliphatic polyamine is tetraethylene pentamine.

5. Oil-soluble additive as defined by claim 1, wherein said aliphatic polyamine is diethylene triamine.

* * * * *